US011497826B2

(12) United States Patent
Romiti

(10) Patent No.: US 11,497,826 B2
(45) Date of Patent: Nov. 15, 2022

(54) METHOD AND APPARATUS FOR RV/MARINE TOILET BOWL SEAL CONDITIONING AND ODOR CONTROL

(71) Applicant: Scott Romiti, Boerne, TX (US)

(72) Inventor: Scott Romiti, Boerne, TX (US)

( * ) Notice: Subject to any disclaimer, the term of this patent is extended or adjusted under 35 U.S.C. 154(b) by 309 days.

(21) Appl. No.: 16/887,768

(22) Filed: May 29, 2020

(65) Prior Publication Data
US 2020/0376150 A1 Dec. 3, 2020

Related U.S. Application Data

(60) Provisional application No. 62/855,100, filed on May 31, 2019.

(51) Int. Cl.
A61L 9/05 (2006.01)
B60R 15/04 (2006.01)
F16L 55/11 (2006.01)

(52) U.S. Cl.
CPC .............. A61L 9/05 (2013.01); B60R 15/04 (2013.01); F16L 55/1141 (2013.01)

(58) Field of Classification Search
CPC ...................................... A61L 9/05
USPC ............ 422/5, 1; 512/1–27; 424/65, 76.1; 62/78, 331
See application file for complete search history.

(56) References Cited

U.S. PATENT DOCUMENTS

| 3,840,914 | A | * | 10/1974 | Tufts | E03D 9/022 4/225.1 |
| 3,846,847 | A | * | 11/1974 | Tufts | B63B 29/16 4/317 |
| 5,142,707 | A | * | 9/1992 | Prue | E03D 9/02 222/522 |
| 6,000,067 | A | * | 12/1999 | Cascia | B60R 15/04 4/223 |
| 2004/0006816 | A1 | * | 1/2004 | Jones | E03D 11/00 4/295 |

* cited by examiner

Primary Examiner — Lori L Baker
(74) Attorney, Agent, or Firm — Taboada Law Firm, PLLC; John M. Taboada

(57) ABSTRACT

A method and apparatus for conditioning an RV/Marine toilet bowl seal, including providing an apparatus comprising a plug comprising a handle portion; and a solid foam coupled to the handle portion; wherein the handle portion is configured to allow a user to insert or remove the solid foam of the plug from a discharge opening of an RV/Marine toilet bowl; and wherein the solid foam is configured to make contact with at least a portion of the RV/Marine toilet bowl seal; pouring a conditioner into the discharge opening of the RV/Marine toilet bowl; inserting the plug into the discharge opening of the RV/Marine toilet bowl such that the solid foam contacts with at least a portion of the RV/Marine toilet bowl seal; and rotating the plug by about a quarter of a turn.

20 Claims, 9 Drawing Sheets

METHOD AND APPARATUS FOR RV/MARINE TOILET BOWL SEAL CONDITIONING AND ODOR CONTROL

I. CROSS REFERENCE TO RELATED APPLICATIONS

This application claims the benefit of the filing date of U.S. Provisional Patent Application Ser. No. 62/855,100, filed on May 31, 2019, entitled "Method and Apparatus for RV/Marine Toilet Bowl Seal Conditioning and Odor Control," the entire disclosure of which is hereby incorporated by reference into the present disclosure.

II. BACKGROUND

The present invention pertains to RV/Marine toilets. More particularly, the invention relates to a method and apparatus to condition an RV/Marine toilet bowl seal and to control odor emanating from the RV/Marine toilet.

III. SUMMARY

In one respect, disclosed is an apparatus for conditioning an RV/Marine toilet bowl seal comprising: a plug comprising: a handle portion; and a solid foam coupled to the handle portion; wherein the handle portion is configured to allow a user to insert or remove the solid foam of the plug from a discharge opening of an RV/Marine toilet bowl; and wherein the solid foam is configured to make contact with at least a portion of the RV/Marine toilet bowl seal.

In another respect, disclosed is a method for conditioning an RV/Marine toilet bowl seal, the method comprising: providing an apparatus comprising: a plug comprising: a handle portion; and a solid foam coupled to the handle portion; wherein the handle portion is configured to allow a user to insert or remove the solid foam of the plug from a discharge opening of an RV/Marine toilet bowl; and wherein the solid foam is configured to make contact with at least a portion of the RV/Marine toilet bowl seal; pouring a conditioner into the discharge opening of the RV/Marine toilet bowl; and inserting the plug into the discharge opening of the RV/Marine toilet bowl such that the solid foam contacts with at least a portion of the RV/Marine toilet bowl seal.

In yet another respect, disclosed is a method for conditioning an RV/Marine toilet bowl seal, the method comprising: providing an apparatus comprising: a plug comprising: a handle portion; and a solid foam coupled to the handle portion; wherein the handle portion is configured to allow a user to insert or remove the solid foam of the plug from a discharge opening of an RV/Marine toilet bowl; and wherein the solid foam is configured to make contact with at least a portion of the RV/Marine toilet bowl seal; loading the solid foam with a conditioner; and inserting the plug into the discharge opening of the RV/Marine toilet bowl such that the solid foam contacts with at least a portion of the RV/Marine toilet bowl seal.

Numerous additional embodiments are also possible.

IV. BRIEF DESCRIPTION OF THE DRAWINGS

Other objects and advantages of the invention may become apparent upon reading the detailed description and upon reference to the accompanying drawings.

Figure 1:
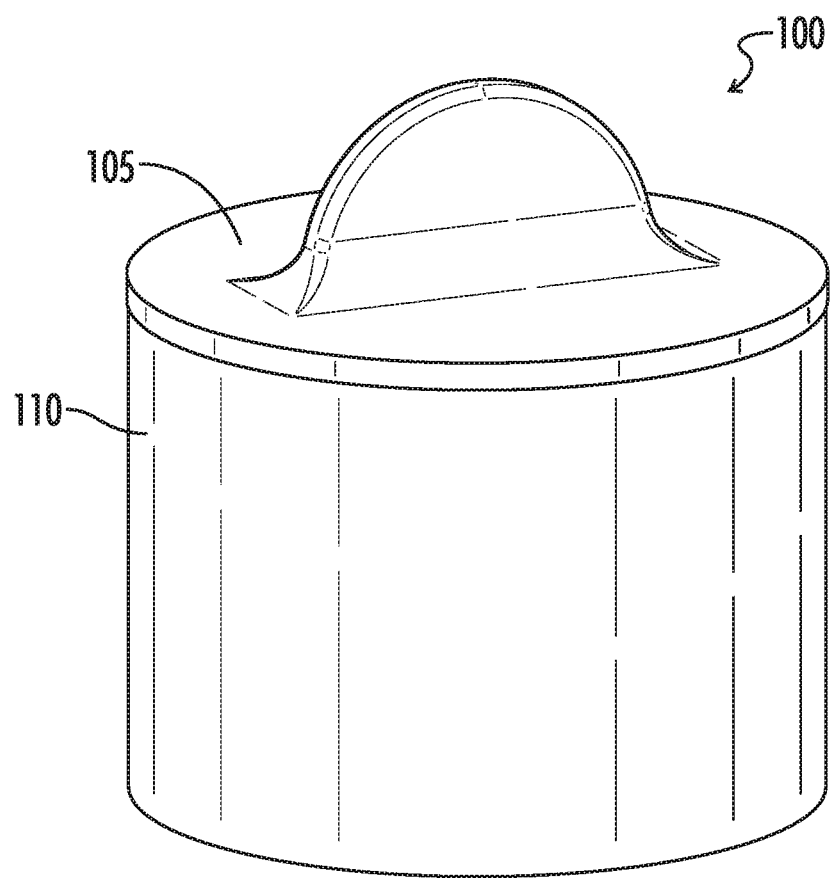
FIG. 1 is a side perspective view of an apparatus for RV/Marine toilet bowl seal conditioning and odor control, in accordance with some embodiments.

While the invention is subject to various modifications and alternative forms, specific embodiments thereof are shown by way of example in the drawings and the accompanying detailed description. It should be understood, however, that the drawings and detailed description are not intended to limit the invention to the particular embodiments. This disclosure is instead intended to cover all modifications, equivalents, and alternatives falling within the scope of the present invention as defined by the appended claims.

V. DETAILED DESCRIPTION

One or more embodiments of the invention are described below. It should be noted that these and any other embodiments are exemplary and are intended to be illustrative of the invention rather than limiting. While the invention is widely applicable to different types of systems, it is impossible to include all of the possible embodiments and contexts of the invention in this disclosure. Upon reading this disclosure, many alternative embodiments of the present invention will be apparent to persons of ordinary skill in the art.

Many RV/Marine toilets comprise a base portion, a bowl portion mounted to the base and having a discharge opening at the lower end of the bowl, a bowl valve at the discharge opening, and a sealing member configured to seal the bowl to the base and to wipe the bowl valve during the flushing of the toilet. The sealing member is also effective in trapping the odors from the base portion of the toilet from escaping into the bowl portion and ultimately into the RV or boat. Unfortunately, the effectiveness of the sealing member degrades over time, due to the drying and cracking of the seal from aging, as well as to improper maintenance due to the use of petroleum based lubricants which break down the seal.

A need exists for a method and apparatus for maintenance and conditioning of the seal as well as for odor control. The embodiment or embodiments described herein solve these problems and others by proposing a new method and apparatus to condition an RV/Marine toilet bowl seal and to control odor emanating from the RV/Marine toilet.

FIG. 1 is a side perspective view of an apparatus for RV/Marine toilet bowl seal conditioning and odor control, in accordance with some embodiments.

Figure 2:
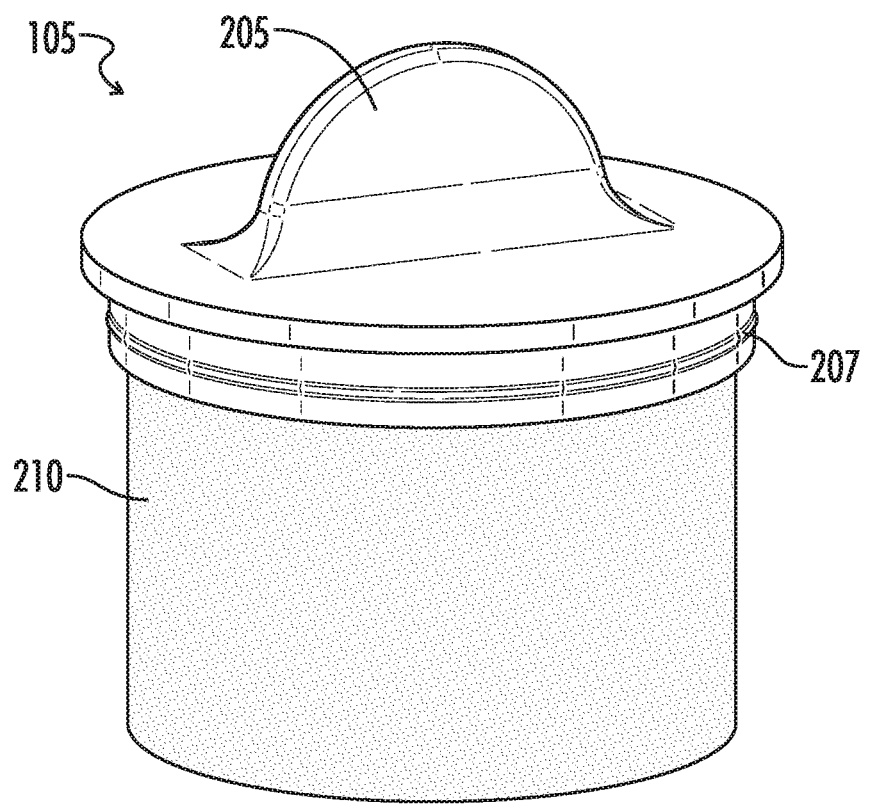
FIG. 2 is a side perspective view of the plug of the apparatus for RV/Marine toilet bowl seal conditioning and odor control, in accordance with some embodiments.

FIG. 2 is a side perspective view of the plug of the apparatus for RV/Marine toilet bowl seal conditioning and odor control, in accordance with some embodiments.

Figure 3:
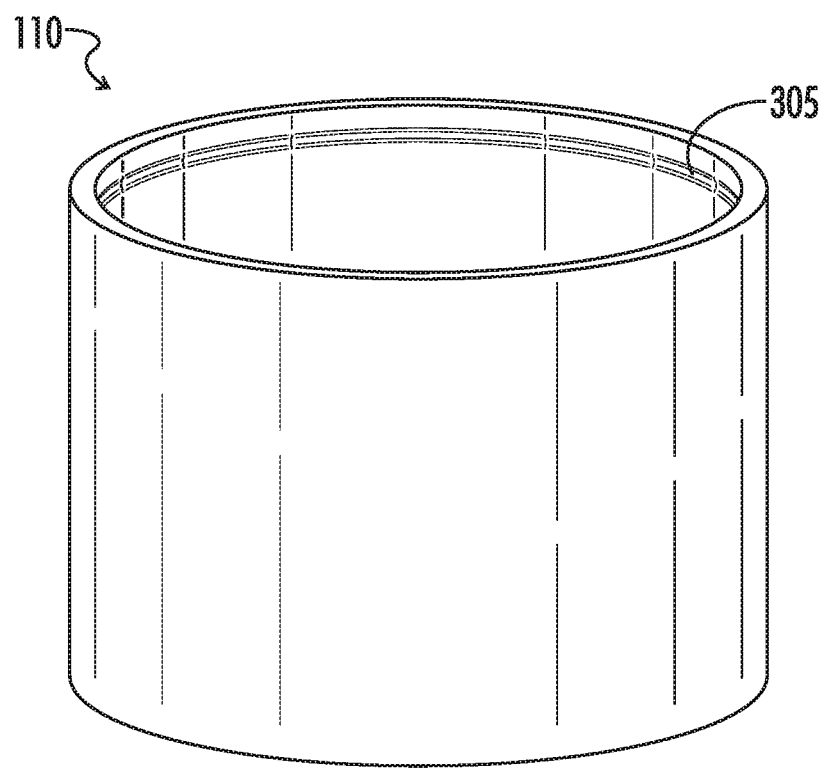
FIG. 3 is a side perspective view of the storage housing of the apparatus for RV/Marine toilet bowl seal conditioning and odor control, in accordance with some embodiments.

FIG. 3 is a side perspective view of the storage housing of the apparatus for RV/Marine toilet bowl seal conditioning and odor control, in accordance with some embodiments.

Figure 4:
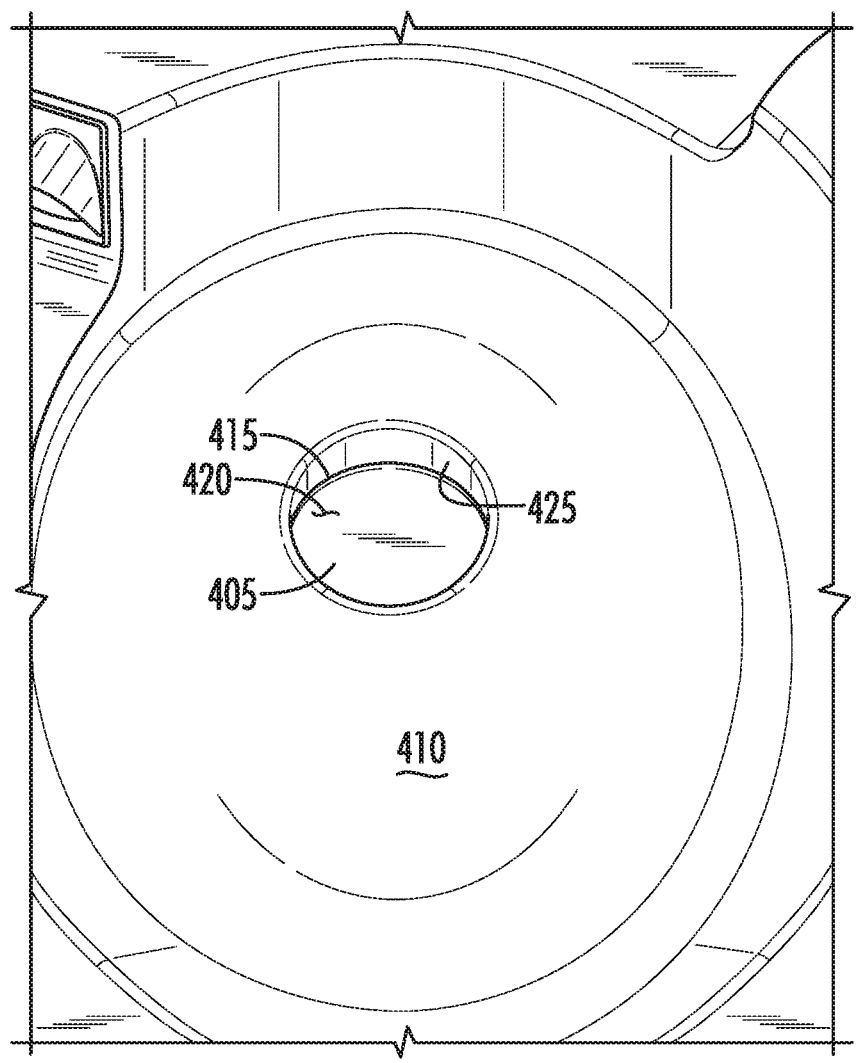
FIG. 4 is a top perspective view of a bowl of an RV/Marine toilet, in accordance with some embodiments.

FIG. 4 is a top perspective view of a bowl of an RV/Marine toilet, in accordance with some embodiments.

Figure 5:
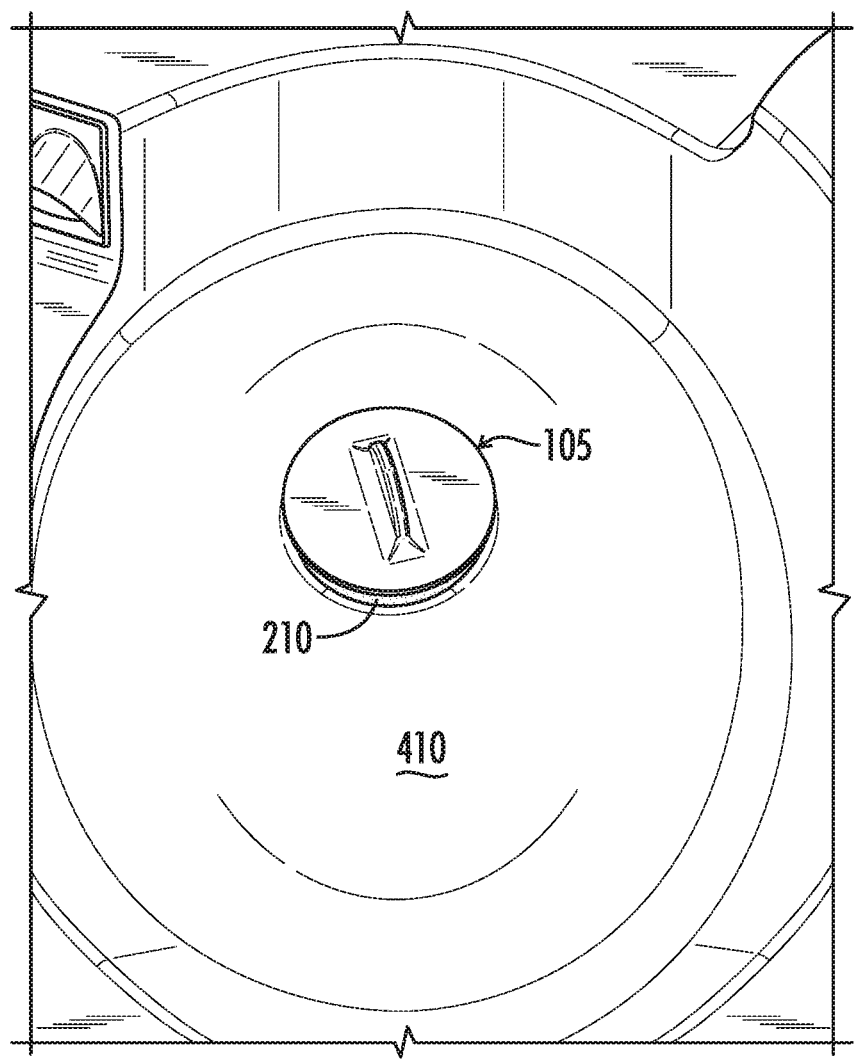
FIG. 5 is a top perspective view of the bowl of an RV/Marine toilet with the installed apparatus for RV/Marine toilet bowl seal conditioning and odor control, in accordance with some embodiments.

FIG. 5 is a top perspective view of the bowl of an RV/Marine toilet with the installed apparatus for RV/Marine toilet bowl seal conditioning and odor control, in accordance with some embodiments.

Figure 6:
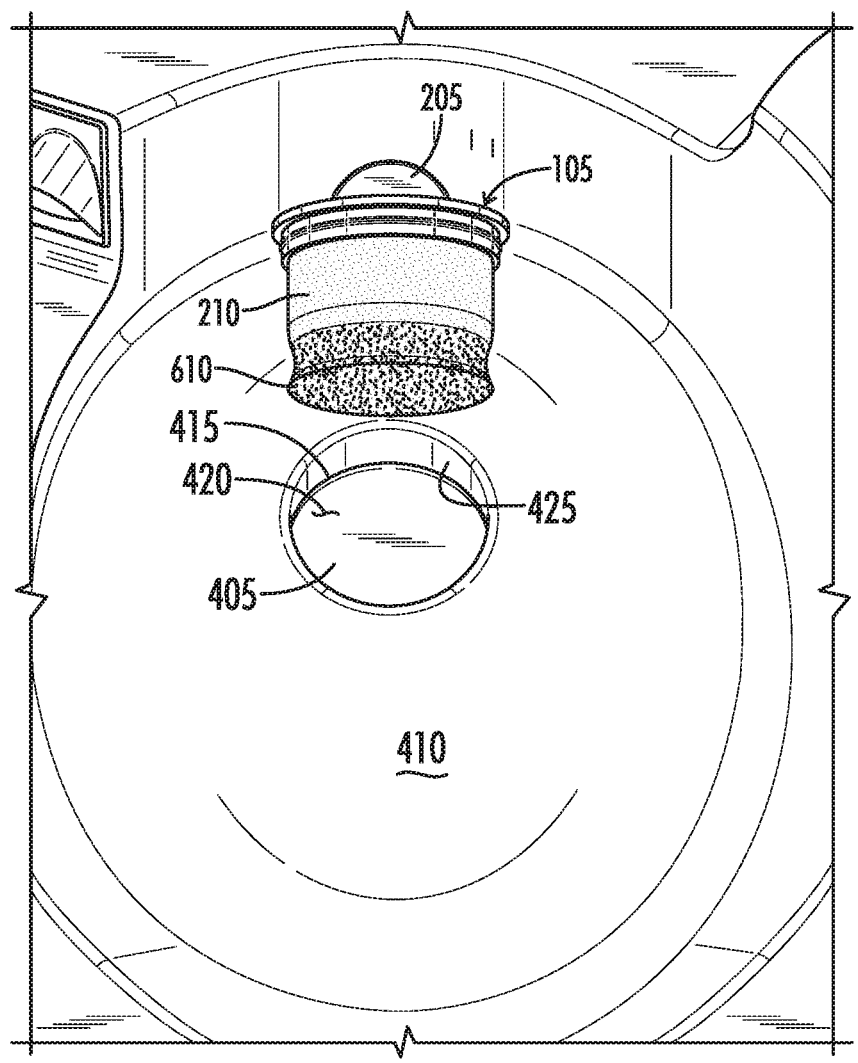
FIG. 6 is a side perspective view of the apparatus for RV/Marine toilet bowl seal conditioning and odor control removed from the discharge opening of an RV/Marine toilet, in accordance with some embodiments.

FIG. 6 is a side perspective view of the apparatus for RV/Marine toilet bowl seal conditioning and odor control removed from the discharge opening of an RV/Marine toilet, in accordance with some embodiments.

Figure 7:
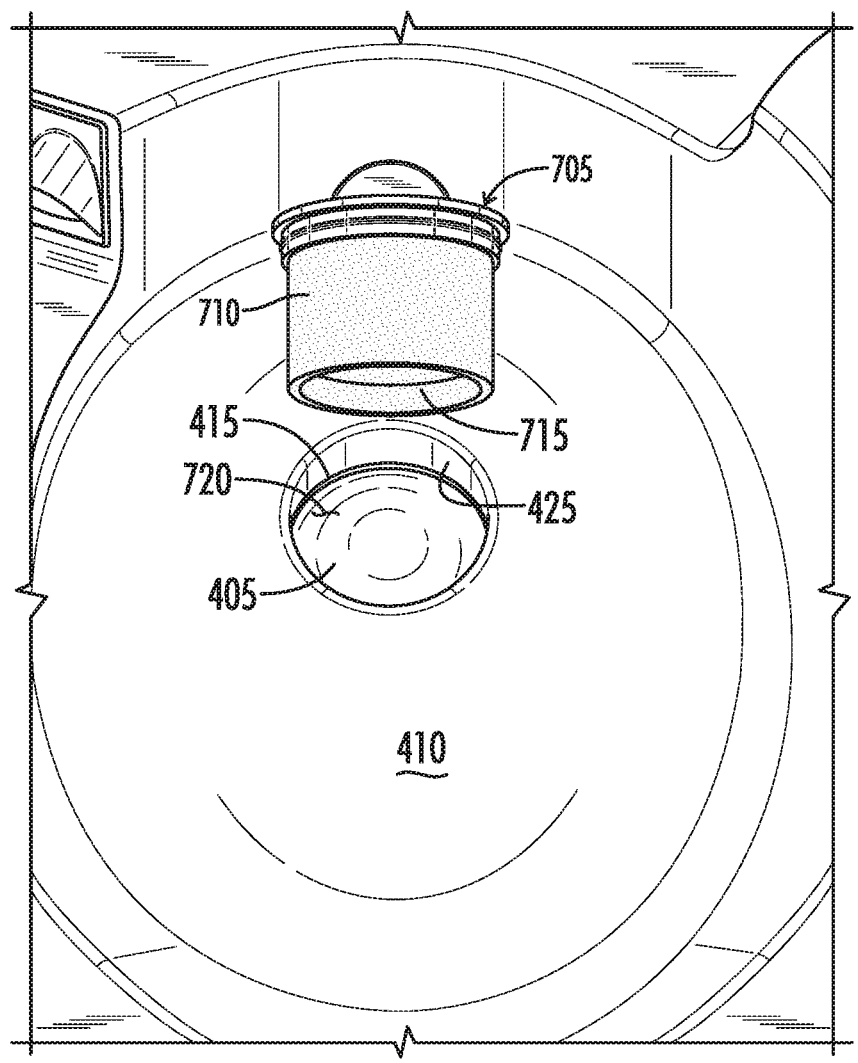
FIG. 7 is a side perspective view of the apparatus for RV/Marine toilet bowl seal conditioning and odor control removed from the discharge opening of an RV/Marine toilet, in accordance with some embodiments.

FIG. 7 is a side perspective view of the apparatus for RV/Marine toilet bowl seal conditioning and odor control removed from the discharge opening of an RV/Marine toilet, in accordance with some embodiments.

In some embodiments, the apparatus 100 for RV/Marine toilet bowl seal conditioning and odor control comprises a plug 105 and a storage housing 110 for the plug. The plug 105 comprises a handle portion 205 configured to allow a user to easily insert or remove the plug from the discharge opening 405 of the RV/Marine toilet bowl 410 and a solid foam 210 coupled to the handle portion. In some embodiments, the solid foam 210 comprises an open-cell structured foam which is capable of absorbing a conditioner 610 which conditions the RV/Marine toilet bowl seal 415 and prevents unwanted odors from coming up into the RV or boat when the solid foam portion of the plug 105 is inserted into the discharge opening of the RV/Marine toilet bowl 410. The solid foam 210 is configured to be soft and pliable such that it is capable of making contact with the RV/Marine toilet bowl valve 420 and toilet bowl seal 415 as well as sealing against the walls 425 of the discharge opening 405. Other materials besides open-cell structured foam may be used as long as the material is capable of absorbing a conditioner. The conditioner loaded into the solid foam may comprise any lubricant such as Thetford® toilet seal lubricant and conditioner, OUTHOUSE® toilet seal conditioner, or the like. FIG. 4 shows a closed flat valve 420 in contact with the RV/Marine toilet bowl seal 415. To load conditioner onto the solid foam, anywhere from about 1 oz. to about 2 oz. of conditioner may be poured into the discharge opening 405. If the RV/Marine toilet bowl seal is not sealing, then about 2 oz. of conditioner may be used. If the RV/Marine toilet bowl is sealing and the RV/Marine toilet is just being prepared for storage or winterizing, then just about 1 oz. of conditioner may be used. After the conditioner is poured into the discharge opening, the solid foam portion of the plug is inserted into the discharge opening as illustrated in FIG. 5. After insertion, the solid foam absorbs the conditioner. In some embodiments, the plug may be rotated by about a quarter of a turn to ensure that the solid foam is fully inserted into the discharge opening and in contact with the toilet bowl seal. When fully inserted, the solid foam will also be in contact with toilet bowl valve 420 and sealed against the walls 425 of the discharge opening 405. To remove the plug 105 from the toilet bowl, a user may pull up on the handle portion 205 to free the plug from the discharge opening. FIG. 6 shows a portion of the solid foam 210 that has absorbed the conditioner 610. Since the solid foam may be made from a soft and pliable material, the solid foam may conform to the shape of the discharge opening.

In some embodiments, the apparatus 100 for RV/Marine toilet bowl seal conditioning and odor control may comprise a securing feature. In one such embodiment, the plug 105 further comprises a ridge 207 on a portion of the plug that is inserted into the storage housing and the storage housing 110 further comprises a recess 305 configured to receive the ridge of the plug. When the plug is inserted into the storage housing, the ridge accommodated into the recess will provide some security from the plug from easily falling out of the storage housing. In some embodiments, the discharge opening of the RV/Marine toilet bowl may comprise a recess similar to that of the storage container in order to secure the plug within the discharge opening. In alternate embodiments, the securing feature may be accomplished through any methods known in the art for securing two individual components together, such as (but not limited to) a screw thread or magnet.

In some embodiments, the RV/Marine toilet bowl may have a ball valve 720 as shown in FIG. 7. In such an embodiment, the plug 705 comprises a solid foam 710 having an cavity 715 at the bottom in order to be able to accommodate a portion of the ball valve 720 so that the solid foam 710 will be able to make contact with the RV/Marine toilet bowl seal 415 when fully inserted into the discharge opening 405. In some embodiments, the cavity may be shaped to conform with the shape of the ball valve. The solid foam 710 of the plug 705 shown in FIG. 7 does not have any conditioner absorbed into the solid foam.

Alternatively, in some embodiments, the apparatus 100 for RV/Marine toilet bowl seal conditioning and odor control is formed of a monolithic piece of absorbent material, such as (but not limited to) open-cell structured foam, and the like, all of which are well known in the art for absorption of liquid and gel matter. In such an embodiment, the plug is unibody, with the handle portion and the solid foam made of a single piece of material.

In some embodiments, the solid foam may be removably coupled to the handle portion of the plug. In such an embodiment, the solid foam may be replaced if it deteriorates over time and the handle portion may be reused with a new solid foam.

Figure 8:
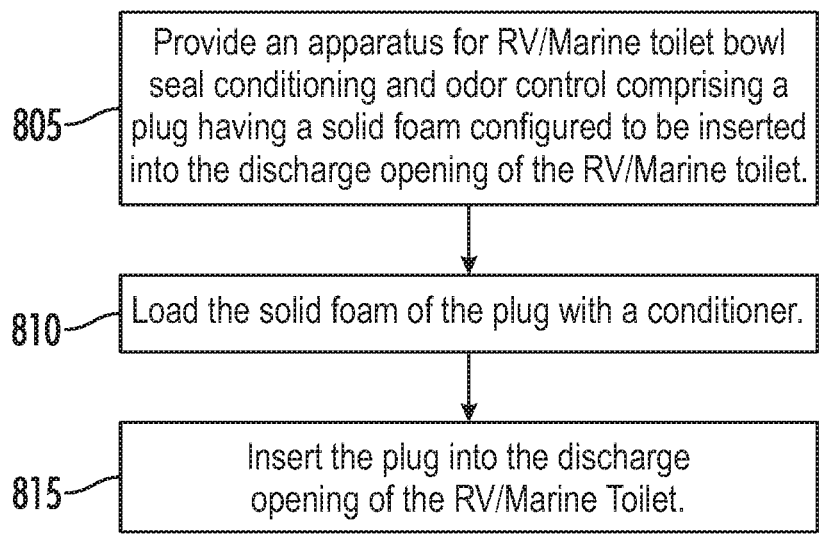
FIGS. 8 and 9 are flowcharts illustrating methods for RV/Marine toilet bowl seal conditioning and odor control using the apparatus illustrated in FIG. 1, FIG. 2, FIG. 5, FIG. 6, and FIG. 7, in accordance with some embodiments.
Figure 9:
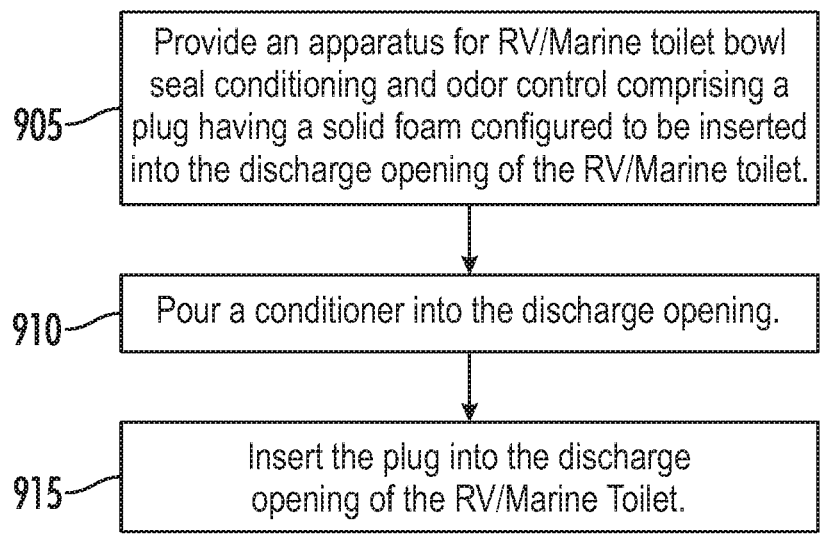

FIGS. 8 and 9 are flowcharts illustrating methods for RV/Marine toilet bowl seal conditioning and odor control using the apparatus illustrated in FIG. 1, FIG. 2, FIG. 5, FIG. 6, and FIG. 7, in accordance with some embodiments.

According to one embodiment of the present invention illustrated in FIG. 8, the method for RV/Marine toilet bowl seal conditioning and odor control begins at block 805, where an apparatus for RV/Marine toilet bowl seal conditioning and odor control is provided, wherein the apparatus for RV/Marine toilet bowl seal conditioning and odor control comprises a plug having a solid foam configured to be inserted into the discharge opening of the RV/Marine toilet. In some embodiments, the plug further comprises a handle portion coupled to the solid foam to allow a user to easily insert or remove the plug from the discharge opening. When the plug is not being used, the plug may be stored in a storage housing sized to accommodate the plug. Next, at block 810, the user loads the solid foam of the plug with a conditioner. The solid foam absorbs the conditioner which will be used to condition the RV/Marine toilet bowl seal as well as provide for additional blocking of the odors from the base portion of the RV/Marine toilet. The conditioner loaded into the solid foam may comprise any lubricant such as Thetford® toilet seal lubricant and conditioner, OUT- HOUSE® toilet seal conditioner, or the like. At block 815, the user inserts the plug into the discharge opening of the RV/Marine toilet. The solid foam loaded with the conditioner allows the conditioner to penetrate and coat the RV/Marine toilet bowl seal and prevent it from being damaged. Additionally, since the integrity of the RV/Marine toilet bowl seal is maintained as well as the contact between the solid foam and the walls of the discharge opening, odors from the base of the RV/Marine toilet are not able to escape into the RV or boat. In some embodiments, the plug may be rotated by about a quarter of a turn to ensure that the solid foam is fully inserted into the discharge opening and in contact with the toilet bowl seal.

In an alternate embodiment illustrated in FIG. 9, the method for RV/Marine toilet bowl seal conditioning and odor control begins at block 905, where an apparatus for RV/Marine toilet bowl seal conditioning and odor control is provided, wherein the apparatus for RV/Marine toilet bowl seal conditioning and odor control comprises a plug having a solid foam configured to be inserted into the discharge opening of the RV/Marine toilet. In some embodiments, the plug further comprises a handle portion coupled to the solid foam to allow a user to easily insert or remove the plug from the discharge opening. When the plug is not being used, the plug may be stored in a storage housing sized to accommodate the plug. Next, at block 910, the user pours a conditioner into the discharge opening. Anywhere from about 1 oz. to about 2 oz. of conditioner may be poured into the discharge opening. If the RV/Marine toilet bowl seal is not sealing, then about 2 oz. of conditioner may be used. If the RV/Marine toilet bowl is sealing and the RV/Marine toilet is just being prepared for storage or winterizing, then just about 1 oz. of conditioner may be used. The conditioner may comprise any lubricant such as Thetford® toilet seal lubricant and conditioner, OUTHOUSE® toilet seal conditioner, or the like. After the conditioner is poured into the discharge opening, at block 915, the user inserts the plug into the discharge opening of the RV/Marine toilet. The solid foam then absorbs the conditioner. In some embodiments, the plug may be rotated by about a quarter of a turn to ensure that the solid foam is fully inserted into the discharge opening and in contact with the toilet bowl seal. When fully inserted, the solid foam will also be in contact with toilet bowl valve and sealed against the walls of the discharge opening. The solid foam, with the absorbed conditioner penetrates and coats the RV/Marine toilet bowl seal and prevents it from being damaged. Additionally, since the integrity of the RV/Marine toilet bowl seal is maintained as well as the contact between the solid foam and the walls of the discharge opening, odors from the base of the RV/Marine toilet are not able to escape into the RV or boat.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The benefits and advantages that may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions, and improvements to the embodiments described above are possible. It is contemplated that these variations, modifications, additions, and improvements fall within the scope of the invention as detailed within the following claims.

The invention claimed is:

1. An apparatus for conditioning an RV/Marine toilet bowl seal comprising:
   a plug comprising:
      a handle portion; and
      a solid foam coupled to the handle portion;
   wherein the handle portion is configured to allow a user to insert or remove the solid foam of the plug from a discharge opening of an RV/Marine toilet bowl; and
   wherein the solid foam is configured to make contact with at least a portion of the RV/Marine toilet bowl seal.

2. The apparatus of claim 1, further comprising a storage housing configured to receive the solid foam and at least a portion of the handle portion.

3. The apparatus of claim 2, wherein the at least a portion of the handle portion comprises a ridge and wherein the storage housing comprises an inner wall having a recess into the inner wall configured to receive the ridge of the at least a portion of the handle portion in order to secure the plug into the storage housing.

4. The apparatus of claim 1, wherein the solid foam is further configured to make contact with a valve of the RV/Marine toilet bowl.

5. The apparatus of claim 1, wherein the solid foam is further configured to seal against walls of the discharge opening of the RV/Marine toilet bowl.

6. The apparatus of claim 1, wherein the solid foam comprises an absorbent material.

7. The apparatus of claim 6, wherein the absorbent material comprises an open-cell structured foam.

8. The apparatus of claim 1, wherein the plug is unibody.

9. The apparatus of claim 1, wherein the solid foam is removably coupled to the handle portion.

10. A method for conditioning an RV/Marine toilet bowl seal, the method comprising:
   providing an apparatus comprising:
      a plug comprising:
         a handle portion; and
         a solid foam coupled to the handle portion;
      wherein the handle portion is configured to allow a user to insert or remove the solid foam of the plug from a discharge opening of an RV/Marine toilet bowl; and
      wherein the solid foam is configured to make contact with at least a portion of the RV/Marine toilet bowl seal;
   pouring a conditioner into the discharge opening of the RV/Marine toilet bowl; and inserting the plug into the discharge opening of the RV/Marine toilet bowl such that the solid foam contacts with at least a portion of the RV/Marine toilet bowl seal.

11. The method of claim 10, further comprising rotating the plug by about a quarter of a turn.

12. The method of claim 10, wherein the apparatus further comprises a storage housing configured to receive the solid foam and at least a portion of the handle portion.

13. The method of claim 12, wherein the at least a portion of the handle portion comprises a ridge and wherein the storage housing comprises an inner wall having a recess into the inner wall configured to receive the ridge of the at least a portion of the handle portion in order to secure the plug into the storage housing.

14. The method of claim 10, wherein the solid foam is further configured to make contact with a valve of the RV/Marine toilet bowl.

15. The method of claim 10, wherein the solid foam is further configured to seal against walls of the discharge opening of the RV/Marine toilet bowl.

16. The method of claim 10, wherein the solid foam comprises an absorbent material.

17. The method of claim 16, wherein the absorbent material comprises an open-cell structured foam.

18. The method of claim 10, wherein the plug is unibody.

19. The method of claim 10, wherein the solid foam is removably coupled to the handle portion.

20. A method for conditioning an RV/Marine toilet bowl seal, the method comprising:
  providing an apparatus comprising:
    a plug comprising:
      a handle portion; and
      a solid foam coupled to the handle portion;
    wherein the handle portion is configured to allow a user to insert or remove the solid foam of the plug from a discharge opening of an RV/Marine toilet bowl; and
    wherein the solid foam is configured to make contact with at least a portion of the RV/Marine toilet bowl seal;
  loading the solid foam with a conditioner; and
  inserting the plug into the discharge opening of the RV/Marine toilet bowl such that the solid foam contacts with at least a portion of the RV/Marine toilet bowl seal.

* * * * *